(12) United States Patent
Shami

(10) Patent No.: US 9,963,112 B2
(45) Date of Patent: May 8, 2018

(54) WINDOW WIPER SYSTEM INCORPORATING WINDOW MOISTURE AND TORQUE SENSORS

(71) Applicant: FORD GLOBAL TECHNOLOGIES, LLC, Dearborn, MI (US)

(72) Inventor: Salman Nazir Shami, Doreen (AU)

(73) Assignee: Ford Global Technologies, LLC, Dearborn, MI (US)

( * ) Notice: Subject to any disclaimer, the term of this patent is extended or adjusted under 35 U.S.C. 154(b) by 637 days.

(21) Appl. No.: 14/481,162

(22) Filed: Sep. 9, 2014

(65) Prior Publication Data
US 2016/0068138 A1    Mar. 10, 2016

(51) Int. Cl.
| B60S 1/08 | (2006.01) |
| G01N 21/47 | (2006.01) |
| G01L 3/10 | (2006.01) |
| B60S 1/48 | (2006.01) |
| B60S 1/02 | (2006.01) |
| G01N 21/43 | (2006.01) |

(52) U.S. Cl.
CPC .............. B60S 1/0837 (2013.01); B60S 1/026 (2013.01); B60S 1/0818 (2013.01); B60S 1/0896 (2013.01); B60S 1/485 (2013.01); G01L 3/102 (2013.01); G01N 21/4738 (2013.01); *B60S 1/486* (2013.01); *B60S 1/488* (2013.01); *G01N 2021/435* (2013.01); *G01N 2021/4709* (2013.01)

(58) Field of Classification Search
CPC ...... B60S 1/0818; B60S 1/0862; B60S 1/485; B60S 1/488; G01N 21/4738; G01N 2021/4709

USPC .......................... 15/250.12; 701/36; 318/444
See application file for complete search history.

(56) References Cited

U.S. PATENT DOCUMENTS

| 5,929,534 A * | 7/1999 | Pickett ................ B60R 16/0237 180/197 |
| 5,929,588 A * | 7/1999 | Shiah ........................ B60S 1/08 318/443 |
| 6,144,906 A * | 11/2000 | Buchanan, Jr. ........ B60S 1/0807 307/9.1 |
| 6,236,180 B1 * | 5/2001 | Contos .................... B60S 1/485 15/250.02 |
| 6,281,649 B1 * | 8/2001 | Ouellette .............. B60S 1/0416 15/250.12 |

(Continued)

FOREIGN PATENT DOCUMENTS

| CN | 202693176 U | 1/2013 |
| DE | 3247016 A1 | 6/1984 |

(Continued)

OTHER PUBLICATIONS

English machine translation for CN202693176.
English machine translation for DE3247016.
English machine translation for DE4332105.

*Primary Examiner* — Michael Jennings
(74) *Attorney, Agent, or Firm* — Jason Rogers; King & Schickli, PLLC

(57) ABSTRACT

A window wiper system includes a wiper assembly, a window moisture sensor, a wiper torque sensor and a control module. The control module is responsive to the window moisture sensor and the torque sensor to control the operation of the window wiper assembly.

5 Claims, 5 Drawing Sheets

(56) References Cited

U.S. PATENT DOCUMENTS

| | | | | |
|---|---|---|---|---|
| 6,422,336 B1* | 7/2002 | Abele | ................ | B62D 6/10 180/446 |
| 6,698,299 B2* | 3/2004 | Cripe | ................ | G01L 3/102 73/862.331 |
| 7,392,565 B2* | 7/2008 | Holbrook | ................ | B60S 1/08 15/250.27 |
| 7,676,880 B2* | 3/2010 | Moein | ................ | B60S 1/08 15/250.12 |
| 2003/0036859 A1* | 2/2003 | Muller | ................ | B60S 1/0818 702/45 |
| 2003/0213087 A1* | 11/2003 | Moein | ................ | B60S 1/0814 15/250.3 |
| 2008/0121489 A1* | 5/2008 | Chevalier | ................ | F16D 3/68 192/105 BB |
| 2008/0147277 A1* | 6/2008 | Lu | ................ | B60W 30/085 701/45 |
| 2009/0282636 A1* | 11/2009 | Braun | ................ | B60S 1/08 15/250.12 |
| 2011/0050148 A1* | 3/2011 | Gao | ................ | H01L 41/1132 318/646 |
| 2012/0266404 A1* | 10/2012 | Braun | ................ | B60S 1/0814 15/250.12 |
| 2013/0103257 A1* | 4/2013 | Almedia | ................ | B60Q 1/143 701/36 |

FOREIGN PATENT DOCUMENTS

| | | |
|---|---|---|
| DE | 4332105 A1 | 3/1995 |
| EP | 1010594 A1 | 6/2000 |
| EP | 2524845 A1 | 11/2012 |
| JP | H02102854 A | 4/1990 |
| WO | 0125064 A1 | 4/2001 |
| WO | 03051693 A1 | 6/2003 |

* cited by examiner

| | Low Torque | Medium Torque | High Torque |
|---|---|---|---|
| High Reflection | Interpretation of Readings: No or low number of drops detected optically, water film detected through torque. Outcome: No delay | Interpretation of Readings: Low number of drops detected optically, windscreen slightly wet, detected through torque sensor. Outcome: High Delay | Interpretation of Readings: Low number of drops detected optically, windscreen dry detected through torque sensor. Outcome: Maximum delay |
| Medium Reflection | Interpretation of Readings: Medium number of drops detected optically, windscreen wet detected through torque sensor. Outcome: Low delay | Interpretation of Readings: Medium number of drops detected optically, windscreen has medium wetness detected through torque sensor. Outcome: Medium delay | Interpretation of Readings: Medium number of drops detected optically, windscreen has high torque so dirt or ice through torque sensor. Outcome: Low delay plus water jet |
| Low Reflection | Interpretation of Readings: High number of drops detected optically, water film detected through torque. Outcome: No delay | Interpretation of Readings: High number of drops detected optically, water film detected through torque or dirt or ice on glass. Outcome: No delay plus hot water jet | Interpretation of Readings: Either dirt ice or snow or water drops detected optically, torque sensor reading rules out water drops. Outcome: High wiper speed, no delay, maximum hot water wiper and turning on of windscreen defogger and de-ice till readings enter a different state. |

Delay types: Zero, Low, Medium, High, Maximum

Optical Sensor Readings

Torque Sensor Readings

FIG. 5

WINDOW WIPER SYSTEM INCORPORATING WINDOW MOISTURE AND TORQUE SENSORS

TECHNICAL FIELD

This document relates generally to the vehicle equipment field and, more particularly, to a window wiper system incorporating a window moisture sensor and a wiper torque sensor which complement each other and provide for enhanced system performance.

BACKGROUND

Automatic windshield wiper control systems that adjust wiper operation/speed to the presence of moisture or the intensity of rainfall on the windshield are well known in the art. Such systems typically include an electronic control module that is connected to the wiper arm drive motor. The control module adjusts the operation and speed of the wiper arm drive motor in response to sensory input.

For over 25 years, prior art automatic window wiper systems have either utilized optical sensors to detect the presence of moisture on the window or torque sensors to detect the resistance to the movement of the wiper blade across the window wherein that resistance has a tendency to decrease with increasing moisture. While these prior art systems have been largely effective for their intended purpose, further improvements in operation are possible.

This document relates to the first automatic window wiper system responsive to sensory input from both a window moisture sensor, such as an optical sensor, and a wiper torque sensor such as one incorporating a plurality of magnetoelastic bands carried on a pivot shaft extending between the wiper arm and the wiper drive motor and a plurality of field sensors that measure differences in magnetic field between the plurality of magnetoelastic bands.

SUMMARY

In accordance with the purposes and benefits described herein, a window wiper system is provided. That system includes a window wiper assembly having a wiper blade, a wiper arm holding the wiper blade and a wiper motor driving the wiper arm. The wiper system further includes a window moisture sensor and a wiper torque sensor. A wiper system control module is responsive to the window moisture sensor and the torque sensor to control operation of the window wiper assembly.

In one possible embodiment the window moisture sensor is an optical sensor. Such an optical sensor includes a light source, a lens for directing light from the light source onto the window to be cleaned by the wiper assembly and a light receptor to detect light from the light source being reflected back from the window.

In one possible embodiment the torque sensor includes a plurality of magnetoelastic bands carried on a pivot shaft extending between the wiper arm and the wiper drive motor as well as a plurality of field sensors that measure the difference in magnetic field between the plurality of magnetoelastic bands as the wiper arm sweeps across the window when driven by the wiper motor.

In one possible embodiment the window wiper system further includes a window heating element wherein the window heating element is also controlled by the control module. In another possible embodiment the system further includes a heated fluid jet cleaning system including a fluid reservoir, a fluid heating element, a nozzle jet and a pump pumping heated fluid from the reservoir through the nozzle onto the window in response to a control signal from the control module.

In accordance with an additional aspect, a method is provided for controlling operation of a windshield wiper assembly to clean a vehicle window. That method may be broadly described as comprising the steps of: (a) detecting, by a window moisture sensor, the presence of moisture on the window, (b) initiating, by a control module, operation of the window wiper assembly, (c) detecting, by a torque sensor, torque on the windshield wiper assembly and (d) adjusting, by the control module, the operation of the windshield wiper assembly in response to detecting window moisture and wiper assembly torque. In one possible embodiment the method further includes activating, by the control module, a window heating element in response to detected window moisture and wiper assembly torque meeting a predetermined criteria. In another possible embodiment the method includes spraying, by the control module, heated fluid onto the window in response to detected window moisture and wiper assembly torque meeting a predetermined criteria. Further the method may include periodically detecting, by the sensors, the presence of moisture on the window and torque on the windshield wiper assembly, comparing by the control module detected values of moisture and torque with predetermined criteria and adjusting, by the control module, operation of the window wiper assembly based upon predetermined criteria.

In one possible embodiment, the window wiper system comprises the window wiper assembly, a wiper torque sensor including a plurality of magnetoelastic bands and a plurality of field sensors and the control module.

In the following description, there is shown and described several preferred embodiments of the window wiper system. As it should be realized, the window wiper system is capable of other, different embodiments and its several details are capable of modification in various, obvious aspects all without departing from the window wiper system as set forth and described in the following claims. Accordingly, the drawings and descriptions should be regarded as illustrative in nature and not as restrictive.

BRIEF DESCRIPTION OF THE DRAWINGS

The accompanying drawings incorporated herein and forming a part of the specification, illustrate several aspects of the window wiper system and together with the description serve to explain certain principles thereof. In the drawings:

FIG. 5 is a block diagram which explains system function and operation.

Reference will now be made in detail to the present preferred embodiments of the window wiper system, examples of which are illustrated in the accompanying drawings.

DETAILED DESCRIPTION

Figure 1:
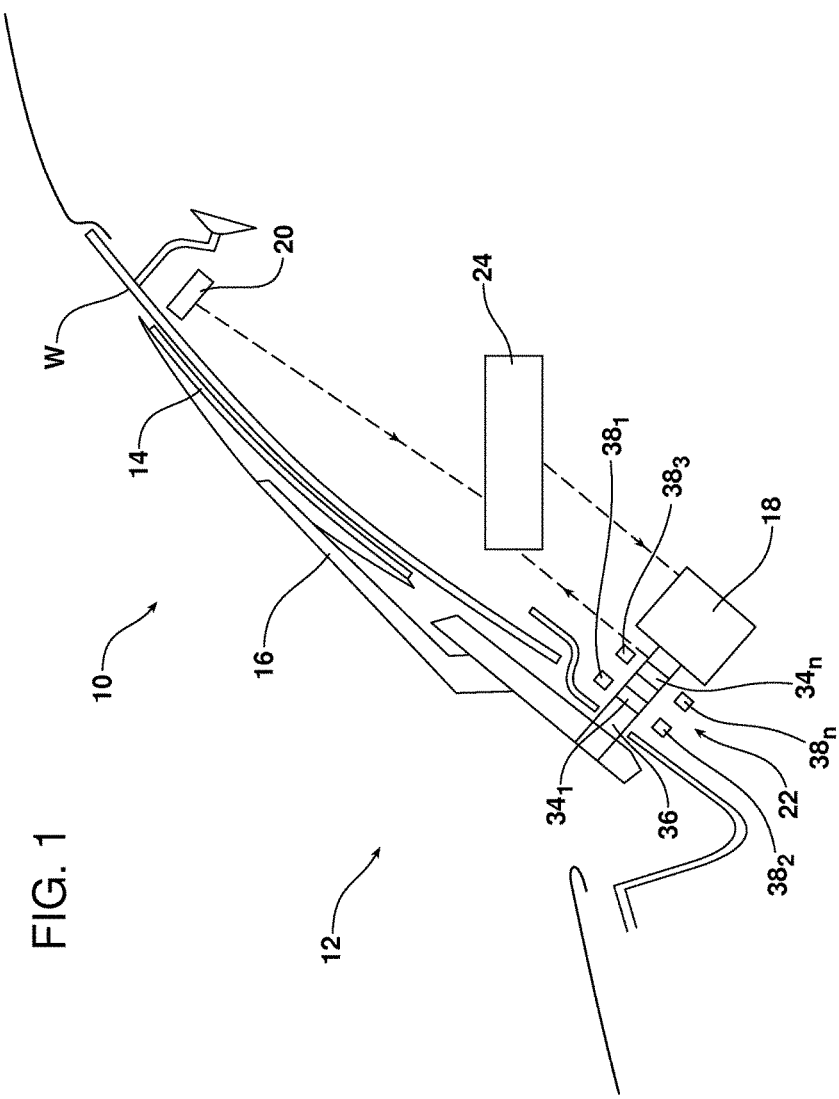
FIG. 1 is a schematical illustration of the window wiper assembly, on a vehicle window, the window moisture sensor, the wiper torque sensor and the control module.

Reference is now made to FIGS. 1-4 which, considered together, illustrate the window wiper system 10. As illustrated in FIG. 1, the window wiper system 10 includes a window wiper assembly 12 comprising a wiper blade 14 that is carried on a wiper arm 16 which is driven by a wiper drive motor 18. The window wiper system 10 also includes a window moisture sensor 20, a wiper torque sensor 22 and a control module or microprocessor 24.

Figure 2:
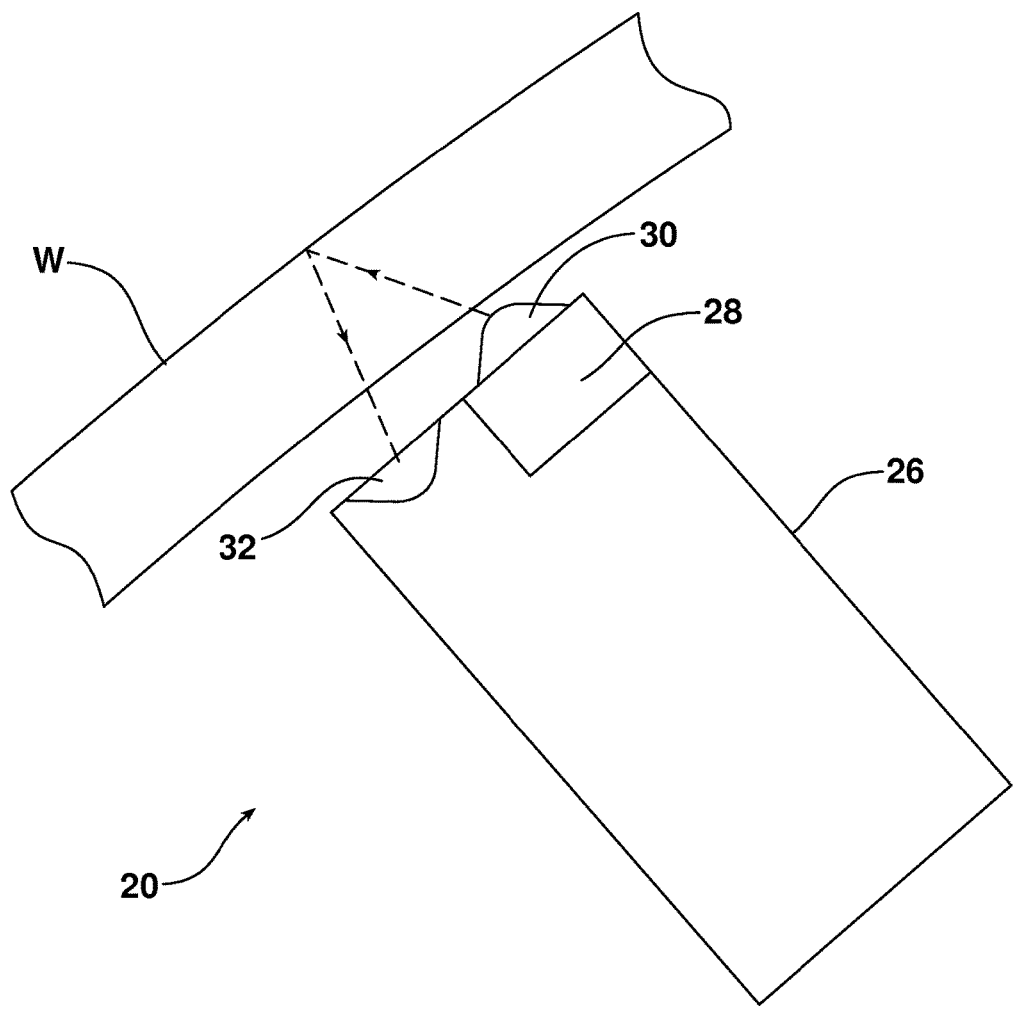
FIG. 2 is a schematical illustration of one possible embodiment of the window moisture sensor.

More specifically, in one possible embodiment illustrated in FIG. 2, the window moisture sensor 20 comprises an optical sensor comprising a housing 26 holding a light source 28. A lens 30 directs light emitted by the light source 28 onto the window W to be cleaned by the window wiper assembly 12 and a light receptor 32 detects light from the light source that is reflected back from the window. The presence of moisture on the window has a tendency to scatter light emitted from the light source 28. Accordingly, as the moisture on the window W increases, the light reflected back and received by the receptor 32 decreases.

Figure 3:
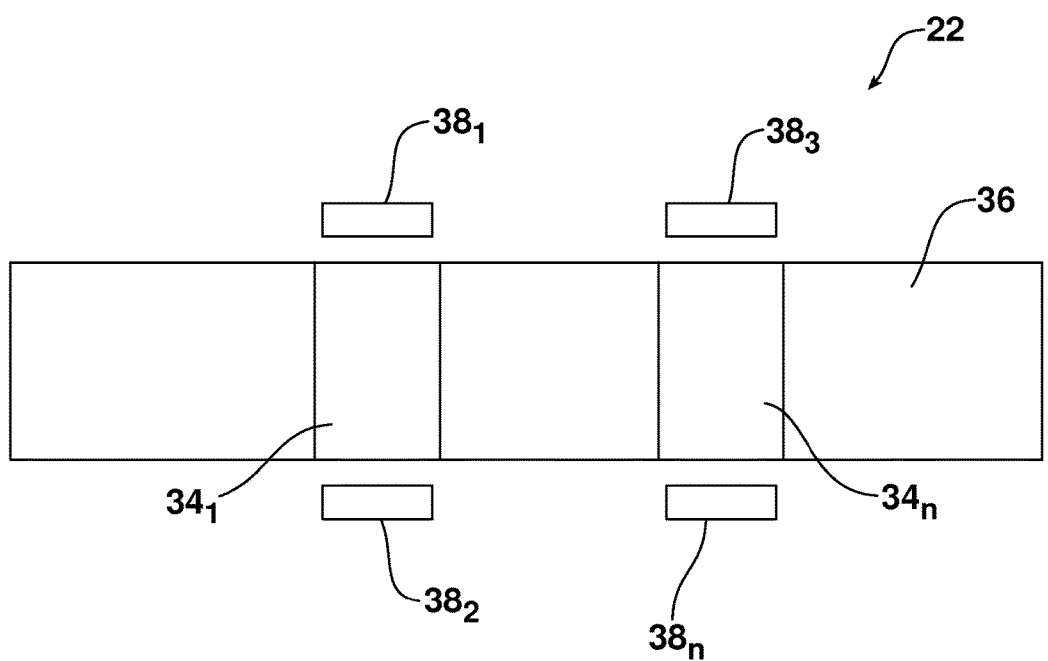
FIG. 3 is a schematical illustration of one possible embodiment of the wiper torque sensor.

As illustrated in FIG. 3, in one possible embodiment of the system 10, the torque sensor 22 includes a plurality of magnetoelastic bands $34_1$-$34_n$ carried on the pivot driveshaft 36 which extends between the wiper motor 18 and the head of the wiper arm 16. In addition, the torque sensor 22 includes a plurality of field sensors $38_1$-$38_n$ carried on the vehicle adjacent the magnetoelastic bands $34_1$-$34_n$. These field sensors $38_1$-$38_n$ measure the differences in magnetic field between the plurality of magnetoelastic bands $34_1$-$34_n$ as the wiper drive motor 18 drives the wiper blade 14 carried by the wiper arm 16. As the amount of moisture on the window W increases, the friction or drag on the wiper blade 14 is reduced and the torque on the pivot arm 36 decreases.

It should be appreciated that an inverse relationship exists between (a) the amount of moisture on the window W and (b) both the amount of light reflected back from the window W to the light receptor 32 and the amount of torque being exerted on the pivot shaft 36 of the window wiper assembly 12. Through extensive testing, predetermined criteria are developed into a lookup table that is used to guide the control module 24 in operation of the window wiper system 10.

Figure 4:
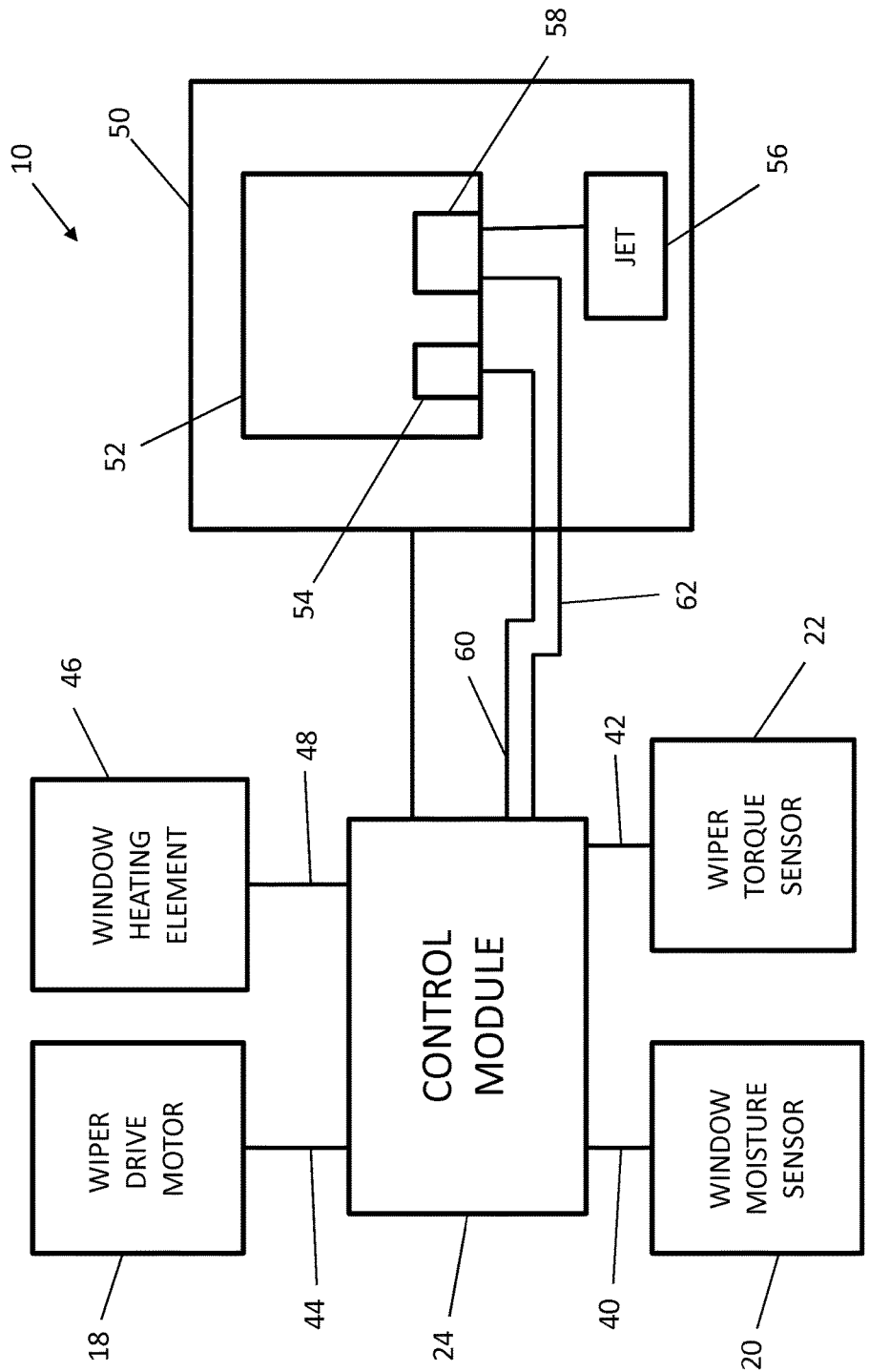
FIG. 4 is a schematical block diagram of the control elements of the window wiper control system.

As illustrated in FIG. 4, the control module 24 is connected to the window moisture sensor 20 by the signal line 40 and to the wiper torque sensor 22 by the signal line 42. Further the control module 24 is connected to the wiper drive motor 18 by the signal line 44.

In one possible embodiment of the invention, the window W includes a window resistance heating element 46 which may be utilized to heat the window W and reduce fog, ice or snow on the window. In this embodiment, the control module 24 controls the operation of the window heating element 46 through the signal line 48.

In another possible embodiment, the system 10 includes a heated fluid jet cleaning subsystem generally designated by reference numeral 50 which includes a fluid reservoir 52, a fluid heating element 54, a nozzle jet 56 and a pump 58. The control module 24 controls the operation of the heating element 54 through the signal line 60 and the operation of the pump 58 through the signal line 62.

Reference is now made to FIG. 5 which schematically illustrates the function and operation of the window wiper system 10. Upon activating the system 10, the window moisture or optical sensor 20 detects the presence of moisture on the window W. More specifically, the sensor 20 emits a light beam from the source 28 and then compares the intensity of the light beam emitted from the source to the intensity of the reflected light detected by the light receptor 32. The resulting light reflectance value gives an indication of the amount of light that was scattered by the moisture or other substances on the window W. The detected light reflectance value is sent through the signal line 40 to the control module 24 which compares that value to predetermined criteria indicating low reflection, medium reflection and high reflection.

At approximately the same time, the control module 24 sends a control signal along line 44 to the wiper drive motor 18 to sweep the window wiper blade 14 held on the wiper arm 16 across the window W one time. As this is done the wiper torque sensor 22 detects the amount of torque being applied to the pivot driveshaft 36. This is accomplished by means of the field sensors $38_1$-$38_n$ which measure the difference in magnetic field between the magnetoelastic bands $34_1$-$34_n$ on the pivot driveshaft 36. The resulting torque value is then sent from the wiper torque sensor 22 through the signal line 42 to the control module 24.

The control module 24 then compares the sensed or detected torque value to predetermined criteria and makes a determination if the detected value falls within the low torque, medium torque or high torque range. The control module 24 then determines the intersection of the detected light reflectance value and the detected torque value and sends an appropriate signal to the wiper drive motor 18 through the signal line 44 so that the wiper system 10 operates with an appropriate delay and/or speed best matched to the driving conditions including, particularly, the presence of moisture and other substances on the window W.

In the event the system 10 is also equipped with the optional window heating element 46, the control module provides, when warranted, an appropriate control signal along line 48 to the window heating element 46 in response to detected conditions based upon data from the sensors 20, 22. Similarly, if the system 10 is equipped with the optional heated fluid jet cleaning subsystem 50, the control module 28 sends an appropriate control signal, when warranted, to the heating element 54 through the control line 60 and the pump 58 through the control line 62 so as to optimize operation of the cleaning subsystem 50 in response to driving conditions as detected by the sensors 20, 22.

In summary, numerous benefits are derived through the operation of the window wiper system 10 and the associated method disclosed herein. More specifically, wiper operation is automatically controlled by the control module 24 in response to input from both a window moisture or optical sensor 20 and a wiper torque sensor 22. Advantageously, the wiper system 10 may operate the window wiper assembly 12 more efficiently and effectively through a combination of optical and torque sensor data than is possible with prior art systems that rely only upon optical data or torque data alone.

For example, one short-coming of an optical sensor 20 is that it only monitors and detects rain over a small surface area of the overall windshield W. Thus, light rain may go undetected for an extended period of time. This may lead to the wipers being prematurely shut off when rainfall begins to lighten after a storm. In this situation, the torque sensor 22 detects the moisture on the windshield W and the data it provides may be used by the control module 24 to properly maintain windshield wiper operation until the rain finally ceases.

It should also be appreciated that data provided from both an optical sensor 20 and a torque sensor 22 allow the control module 24 to more quickly and accurately identify and respond to icy windshield conditions. Ice detection is indicated by a combination of a low torque reading from the torque sensor 22 and a high light scatter reading from the optical sensor 20.

The provision of the optional window heating element 46 and/or optional heated fluid jet cleaning subsystem 50 further enhances the operating capabilities of the system 10 so it may better adjust to and meet the needs of a vehicle operator when presented with various driving conditions including those associated with harsh winter weather.

The foregoing has been presented for purposes of illustration and description. It is not intended to be exhaustive or to limit the embodiments of the window wiper system and associated method to the precise form disclosed. Obvious modifications and variations are possible in light of the above teachings. For example, the window wiper system 10 may incorporate additional sensors to provide still more operating data to the control module 24 which utilizes that data to act accordingly in adjusting the operation of the window wiper assembly 12 including, for example, the operating speed thereof. Such additional sensors include but are not necessarily limited to a vehicle speed sensor, an ambient temperature sensor, an air circulation system temperature sensor and combinations thereof. In another possible embodiment, the window wiper system 10 relies only on the torque sensor 22 including the magnetoelastic bands $34_1$-$34_n$ and the field sensors $38_1$-$38_n$. All such modifications and variations are within the scope of the appended claims when interpreted in accordance with the breadth to which they are fairly, legally and equitably entitled.

What is claimed:

1. A window wiper system, comprising:
   a window wiper assembly including a wiper blade, a wiper arm holding said wiper blade and a wiper motor driving said wiper arm;
   an optical sensor detecting presence of moisture on a window;
   a wiper torque sensor including a plurality of magnetoelastic bands carried on a pivot shaft extending between said wiper arm and said wiper drive motor and a plurality of field sensors that measure differences in magnetic field between said plurality of magnetoelastic bands; and
   a control module responsive to said optical sensor and said wiper torque sensor to control operation of said window wiper assembly.

2. The system of claim 1, wherein said optical sensor includes a light source, a lens for directing light from said light source onto a window to be cleaned by said window wiper assembly and a light receptor to detect light from said light source being reflected back from said window.

3. The system of claim 1, wherein said system further includes a window heating element, said window heating element being controlled by said control module.

4. The system of claim 3, wherein said system further includes a heated fluid jet cleaning subsystem including a fluid reservoir, a fluid heating element, a nozzle jet and a pump for pumping heated fluid from said reservoir through said nozzle onto said window in response to a control signal from said control module.

5. The system of claim 1, wherein said system further includes a heated fluid jet cleaning system including a fluid reservoir, a fluid heating element, a nozzle jet and a pump for pumping heated fluid from said reservoir through said nozzle onto said window in response to a control signal from said control module.

* * * * *